(12) United States Patent
Ghalili et al.

(10) Patent No.: US 11,839,592 B2
(45) Date of Patent: Dec. 12, 2023

(54) CANNABINOID AND MENTHOL TRANSDERMAL DELIVERY SYSTEMS AND METHODS

(71) Applicants: Babak Ghalili, New York, NY (US); Arthur Goldberg, Livingston, NJ (US); John Borja, Keyport, NJ (US)

(72) Inventors: Babak Ghalili, New York, NY (US); Arthur Goldberg, Livingston, NJ (US); John Borja, Keyport, NJ (US)

( * ) Notice: Subject to any disclaimer, the term of this patent is extended or adjusted under 35 U.S.C. 154(b) by 0 days.

(21) Appl. No.: 17/173,381

(22) Filed: Feb. 11, 2021

(65) Prior Publication Data

US 2021/0244684 A1 Aug. 12, 2021

Related U.S. Application Data

(60) Provisional application No. 62/972,824, filed on Feb. 11, 2020.

(51) Int. Cl.
| | | |
|---|---|---|
| *A61K 31/05* | (2006.01) | |
| *A61K 47/06* | (2006.01) | |
| *A61L 15/60* | (2006.01) | |
| *A61F 13/00* | (2006.01) | |
| *A61F 13/51* | (2006.01) | |
| *A61F 13/02* | (2006.01) | |

(52) U.S. Cl.
CPC ........ *A61K 31/05* (2013.01); *A61F 13/00029* (2013.01); *A61F 13/0253* (2013.01); *A61F 13/51* (2013.01); *A61K 47/06* (2013.01); *A61L 15/60* (2013.01); *A61F 2013/00089* (2013.01)

(58) Field of Classification Search
CPC ...... A61K 9/7007; A61K 9/7084; A61K 9/70; A61K 31/05; A61K 47/06; A61F 13/00029; A61F 13/0209; A61F 2013/00089; A61F 13/0253; A61F 13/51; A61P 1/00; A61L 15/60
See application file for complete search history.

(56) References Cited

U.S. PATENT DOCUMENTS

| | | | |
|---|---|---|---|
| 5,869,087 A | | 2/1999 | Hirano et al. |
| 6,620,428 B1 * | | 9/2003 | Hoeck ................. A61K 9/7053 424/449 |
| 6,673,363 B2 * | | 1/2004 | Luo ..................... A61K 8/0208 424/443 |
| 9,839,693 B2 | | 12/2017 | Borja et al. |
| 10,383,908 B1 * | | 8/2019 | Berry ..................... A61K 9/06 |
| 2012/0201891 A1 | | 8/2012 | Cottrell et al. |
| 2013/0281523 A1 | | 10/2013 | Letendre et al. |
| 2016/0184212 A1 | | 6/2016 | Casasanta |
| 2017/0021026 A1 * | | 1/2017 | Naheed .................. A61K 47/44 |
| 2018/0078512 A1 * | | 3/2018 | Weimann ............. A61K 9/7053 |
| 2018/0344676 A1 | | 12/2018 | Hoag |
| 2018/0344860 A1 | | 12/2018 | Naheed |
| 2019/0110981 A1 | | 4/2019 | Weimann |
| 2019/0216745 A1 | | 7/2019 | Song |
| 2019/0231711 A1 | | 8/2019 | Weimann |
| 2019/0247299 A1 | | 8/2019 | Cameron et al. |

OTHER PUBLICATIONS

Alankar, "A Review on Peppermint Oil", Asian Journal of Pharmaceutical and Clinical Research, vol. 2, Issue 2, Apr.-Jun. 2009, 7 pages.
Echo, "What is Full-Spectrum Hemp Oil and Why is it Important?" Published in Education, Overview of Cannabinoids, May 5, 2017, https://echoconnection.org/full-spectrum-hemp-oil-important/, 5 pages.
Krizek et al. "Menthol-based hydrophobic deep eutectic solvents; Towards greener and efficient extraction of phytocannabinoids" Journal of Cleaner Production, Available onling May 10, 2018, http://doi.org/10.1016/j.depro.2018.05.080, 6 pages.
Nunley, "What is Full-Spectrum Hemp Oil?" Medical Marijuana, Inc., Aug. 18, 2019, https://www.medicalmarijuanainc.com/full-spectrum-hemp-oil/, 13 pages.
"Humectants and Moisturizers: What's the Difference?" Skinbetter Science, Dec. 28, 2016, https://skinbetter.com/humectants-moisturizers-difference/, 6 pages.
"Undecylenic acid topical", Cardiology Associates of NNY, Sep. 8, 2017, http://www.cardiologynny.com/PatientPortal/MyPractice.aspx?UAID=%7B16300E1B-EC83-4B13-B3F3-SE33D932B385%7D&ID=HW5d03686a1&Title=Cruex#:~:text=Undeclyenic%20acid%20topical%20is%20used,listed%20in%20medication%20guide, 2 pages.
International Search Report and Written Opinion, United States Patent & Trademark Office, Application No. PCT/US2021/017527, dated Jul. 16, 2021, 22 pages.
Otto et al. "What is the future of heated transdermal delivery systems?" Therapeutic Delivery (2014) vol. 5, issue 9, https://www.future-science.com/doi/pdfplus/10.4155/tde.14.66, ISSN 2041-5990, 4 pages.

* cited by examiner

*Primary Examiner* — Anna R Falkowitz
(74) *Attorney, Agent, or Firm* — ZIEGLER IP LAW GROUP LLC

(57) ABSTRACT

The present disclosure relates to compositions, methods of use and methods of manufacturing of a transdermal delivery systems, patches, vehicles and devices used to relieve pain (i.e., analgesics) and/or inflammation that contain a pharmaceutically effective amount of a pharmaceutically acceptable and effective cannabinoid and menthol.

10 Claims, 11 Drawing Sheets

FIG. 6A
FIG. 6B
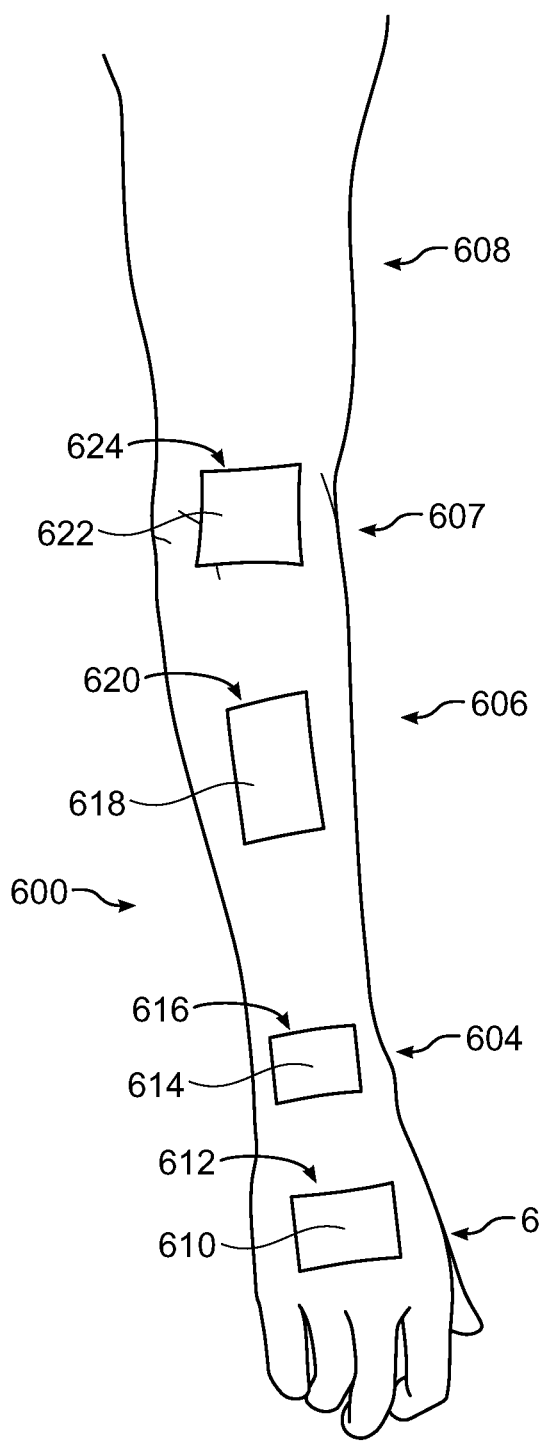
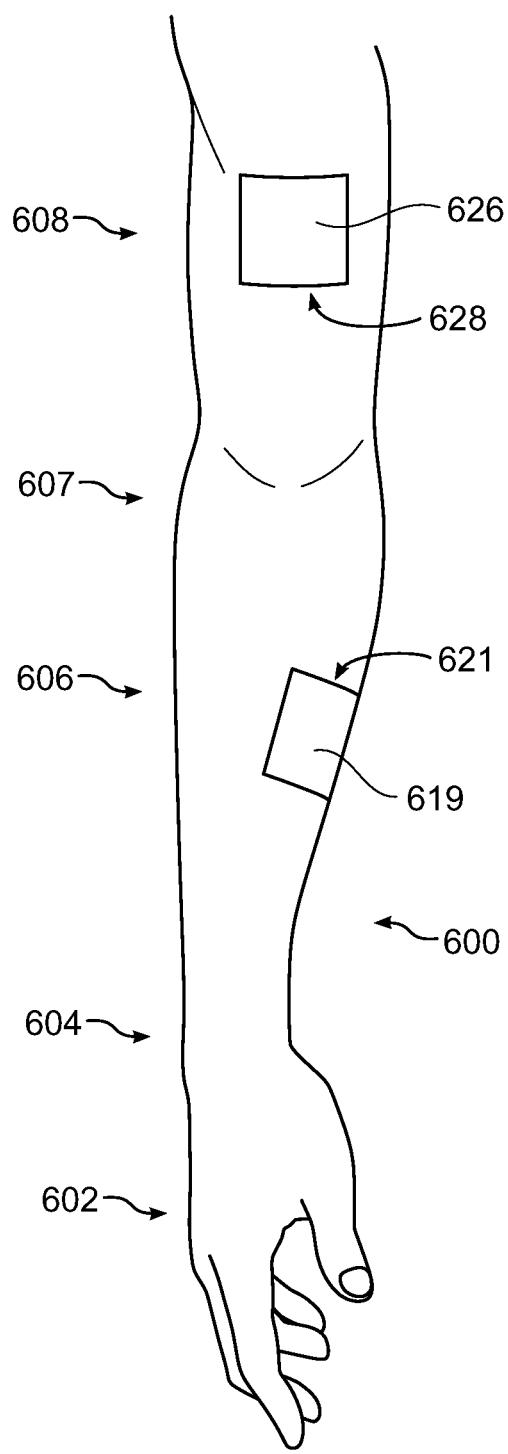

CANNABINOID AND MENTHOL TRANSDERMAL DELIVERY SYSTEMS AND METHODS

CROSS-REFERENCE TO RELATED APPLICATION

This application claims priority to and the benefit of U.S. Provisional Patent Application Ser. No. 62/972,824 filed Feb. 11, 2020, the disclosure of which is incorporated herein by reference in its entirety.

FIELD

The aspects of the present disclosure relate to transdermal delivery systems, patches, vehicles and devices as well as methods of making and using same including pharmaceutically active agents such as cannabinoids and menthol.

BACKGROUND

There is a need for novel treatments for pain and inflammation on various parts of the body. Some current agents may be ineffective and can, for example, come with unacceptable side effects. Furthermore, there is a growing concern about the overuse of opioid pain treatments.

Topical delivery systems, patches, vehicles and devices have been used to deliver of pharmaceutically active agents. However, many such delivery systems, patches, vehicles and devices can have shortcomings such as. Such as drug-in-adhesive systems. Such systems mix the pharmaceutically active agent with the adhesive and can be entrapped, therefore not sufficient enough to get the full dose.

It would be preferable to have a topical delivery system, vehicle and device that would keep separate the pharmaceutically active agents from the patch adhesive system. This will give full contact of the pharmaceutically active agent onto the skin without the hindrance of the adhesive.

SUMMARY

In one embodiment, a transdermal delivery system is provided. The transdermal delivery system comprises an absorbent material including at least one cannabinoid, menthol, a carrier solvent, an absorbent polymer and a surfactant.

In another embodiment, a transdermal delivery system is provided. The transdermal delivery system comprises a backing material, an absorbent material layer and a release layer. The backing material includes a first side and a second side, the second side including a topically acceptable adhesive. The absorbent material layer includes a first side and a second side and wherein the first side of the absorbent material layer is positioned adjacent the second side of the backing material and comprises at least one pharmaceutically active agent, a carrier solvent and an absorbent polymer. The release layer is in contact with a portion of the second side of the backing material. The absorbent material is positioned in a cavity in between the backing layer and the release layer.

In another embodiment, a transdermal delivery system is provided. The transdermal delivery system comprises a backing material, an absorbent material layer and a release layer. The backing material includes a first side and a second side, the second side including a topically acceptable adhesive. The absorbent material layer includes a first side and a second side and wherein the first side of the absorbent material layer is positioned in contact with the second side of the backing material and comprises full spectrum hemp oil, menthol, a carrier solvent and an absorbent polymer. The release layer is in contact with a portion of the second side of the absorbent layer and the second side of the backing material. The absorbent material is positioned in a cavity in between the backing layer and the release layer.

In another embodiment, a method of treating at least one of pain and inflammation of an animal using a transdermal delivery system. The transdermal delivery system comprises at least one cannabinoid, menthol, a carrier solvent, an absorbent polymer and a surfactant. The method comprises topically administering to a body part of the animal the transdermal delivery system.

In another embodiment, a method of treating at least one of pain and inflammation of an animal using a transdermal delivery system. The transdermal delivery system comprises an absorbent material having a first side and a second side, the absorbent material including at least one cannabinoid, menthol a carrier solvent, an absorbent polymer and a surfactant. The method comprises topically applying the first side or the second side of the absorbent material to a skin surface of a body part of the animal.

BRIEF DESCRIPTION OF THE DRAWINGS

The accompanying drawings illustrate presently preferred embodiments of the present disclosure, and together with the general description given above and the detailed description given below, serve to explain the principles of the present disclosure.

FIGS. 6A to 6F illustrate an exemplary implementation of the aspects of the disclosed embodiments.

DETAILED DESCRIPTION

Figure 1:
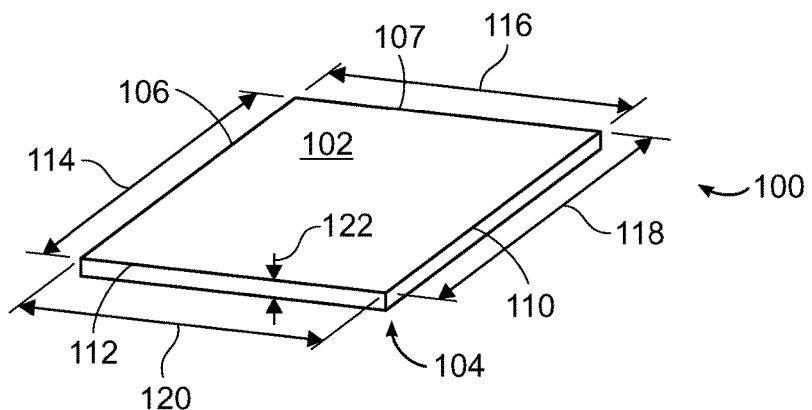
FIG. 1 is a perspective view of an embodiment of the present disclosure.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be per-formed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

The term "pharmaceutically acceptable" means that which is useful in preparing a pharmaceutical composition that is generally non-toxic and is not biologically undesirable and includes that which is acceptable for veterinary use and/or human pharmaceutical use.

The term "topically acceptable" or "dermally acceptable" means the compound, substance or device may be administered to or onto the surface of a patient, including the skin or other accessible tissues, without substantial harmful effects to the body part and/or its surfaces.

As used herein, the term "pharmaceutically active agent" means a composition which, when administered to a human or animal patient, has a biochemical or physiological effect on the patient (i.e., a therapeutic effect or activity).

The delivery systems, patches, vehicles and devices of the present disclosure are also useful in the fields of human medicine for the administration of pharmaceutically active agents to people (i.e., human patients) and in veterinary medicine for the administration of pharmaceutically active agents to animals such as small animals or pets (e.g., dogs, cats, etc.) and large animals (e.g., horses and farm animals (e.g., cows, sheep, etc.)).

Pharmaceutically active agents can include pharmaceutical agents such as analgesics, decongestants, bronchodilators and other antiasthmatic agents, cardiovascular agents such as beta-blockers, ACE inhibitors, diuretics, antithrombics, etc., diabetic agents, antihistamines, anesthetics, antifungals, antinauseants, antiemetics, antibacterial agents, antifungal agents, corticosteroids, neurological agents, anti-inflammatories, vaccines, biological agents (such as Humera, Enbrel and Remicade), wound healing agents and anticonvulsants. Vitamins (particularly A, C, D and E) are a particular embodiment of a pharmaceutically active agent. The concentration of the pharmaceutically active ingredient in embodiments of the present disclosure are dependent on the identity of the pharmaceutically active agent, the condition and patient being treated and the potency desired.

One group of particularly interesting pharmaceutically active agents include pharmaceutical agents that are moisture sensitive such as biologicals, enzymes, proteins (and fragments thereof). Other moisture sensitive pharmaceutical agents include Adderall, alprazolam, gemifloxacin, hydromorphone and zolmitriptan.

Another embodiment of the present disclosure relates to antifungal pharmaceutically active agents such as Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, and Micafungin.

Another embodiment of the present disclosure relates to pharmaceutically active agents for wart removal compounds such as salicylic acids. Such treatments are of specific interest due to heightened response to the anhydrous medium of the hydrogel.

Another embodiment relates to pharmaceutically active agents for wound healing agents and products (such as gauze, bandage, and synthetic skin). Such agents include aloe, benzyl alcohol, coagulants (such as styptic, chitosan, vitamin K, phytomenadione, menadione, etamsylate, carbazochrome Batroxobin), ferric sulfate, ticosan, becaplermin, antimicrobial agents (including antibiotics such as gentamycin, polymyxin B, zinc bacitracin, metronidazole, ofloxacin, minocycline, hydrocortisone, triamcinolone and tetracycline), antifungals, silver, povidone-iodine, polyhexamethylene biguanide, dialkylcarbamoylchloride, lactoferrin, growth factors (such as epidermal growth factor (EGF), platelet derived growth factor (PDGF), fibroblast growth factor (FGF), transforming growth factor (TGF-b1), insulin-like growth factor (IGF-1), human growth hormone, granulocyte macrophage colony stimulating (GM-CSF)).

Another embodiment relates to pharmaceutically active agents for scar healing agents such as vitamins, aloe vera, and benzyl alcohol.

Pharmaceutically active agents can also include cosmetic agents such as caffeine, sunscreens (such as butyl methoxydibenzoylmethane, oxybenzone, bumetrizole, ecamsule, phenylbenzimidazole sulfonic acid, ethylhexyl methoxycinnamate, menthyl anthranilate, octocrylene, para-aminobenzoic acid (PABA), and Tinosorb M), anti-inflammatories (such as salicylates), anti-acne agents (such as (isotretinoin, Benzamycin, clindamycin, Erythromycin, minocycline and tretinoin), vitamins (particularly vitamins C and E, Biotin), ubiquinone, retinoids, Minoxidyl, Zinc pyrithion, ketoconazole, allantoin, herbal extracts (such as Passion Fruit extract (*Passiflora Edulis*), Red rose extract, Raspberry extract (*Rubus idaeus*), Yucca herbal extract, Aloe vera leaf gel, Tea tree oil (*Melaleuca alternifolia*), Peppermint leaf oil, Spearmint leaf oil, Wintergreen leaf oil (*Gaultheria Procumbens*), Lavender oil, Cinnamon leaf oil, Lemon peel oil, Valencia orange peel oil, Pink grapefruit peel oil, Roman chamomile oil (*Anthemis nobilis* Flower Oil), and Jasmine oil), protein hydrolysates (i.e. short protein fragments that are still called "peptides") and skin lightening agents.

One particular cosmetic agent of interest that is a pharmaceutically active agent is coenzyme Q10 (Co Q10), also known as ubiquinone, ubidecarenone, coenzyme Q, and abbreviated at times to CoQ10, CoQ or Q10. Ubiquinone is a 1,4-benzoquinone, where Q refers to the quinone chemical group, and 10 refers to the number of isoprenyl chemical subunits in its tail.

"Pain" as referred to herein for the composition and method embodiments of the current disclosure and for which an analgesic or pain relieving or pain treating composition or component thereof treats includes, but is not limited to local pain, systemic pain, oral pain, dental pain and general pain, regardless of the location on the body to which the embodiment of the current disclosure is administered.

"Anti-inflammatory" as referred to herein for the composition and method embodiments of the current disclosure and for which an anti-inflammatory composition or component thereof treats includes, but is not limited to local inflammation, systemic inflammation, oral inflammation, dental inflammation and general inflammation, regardless of the location on the body to which the embodiment of the current disclosure is administered.

Pharmaceutically active agents can also include exosomes that include cellular materials that naturally occur therein or that have been loaded with other pharmaceutically active agents, including those disclosed herein as well as protein and/or peptide materials including antibodies and fragments thereof.

Other pharmaceutically active agents can include the following class of active ingredients: laxatives, analgesics, antibiotics, antirheumatics, antiallergics, antiarrhythmics, antibiotics, antiepileptics, beta-receptor blockers, calcium channel blockers, chemotherapeutics, enzymes, extracts, inhibitors of the rennin-angiotensin system, broncholytics/ antasthmatics cholinergics, diuretics, circulation promoters, gout agents influenza agents, coronary agents, osteoporosis agents (biphosphonates), lipid reducers, gastrointestinal agents, peptides, proteins, proton pump blockers, psychopharmaceuticals, platelet aggregation inhibitors urological agents venous therapeutic agents, vitamins and minerals.

The aspects of the present disclosure relate to transdermal delivery systems, patches, vehicles and devices as well as methods of use and methods of treatment using same and methods of manufacture of same including pharmaceutically active agents and can be used, for example, to relieve pain (i.e., analgesics) and/or inflammation, methods of making such as transdermal delivery systems, patches, vehicles and devices and methods of using such transdermal delivery systems, patches, vehicles and devices including topically applied (e.g., to skin or another body part) transdermal delivery systems, patches, vehicles and devices including pharmaceutical transdermal delivery systems, patches, vehicles and devices, including analgesic and/or anti-inflammatory pharmaceutical compositions for the treatment of pain and/or inflammation, that contain a pharmaceutically effective amount of more or more than one pharmaceutically active agents, such as, for example, a pharmaceutically acceptable and effective cannabinoid and/or menthol.

The combination of cannabinoid and menthol into a single therapeutic composition, for example, a transdermal delivery system, patch, vehicle or device can provide improved and better focused delivery of the pharmaceutically active agents to a patient than separately applying the cannabinoid and menthol (to different areas of the body or layered one on top of another) without the hydrous hydrogel vehicle.

Transdermal delivery systems, patches, vehicles and devices as well as methods of use and methods of treatment using same and methods of manufacture of same, such as, for example, embodiments of the present disclosure, include transdermal delivery systems, patches, vehicles and devices in a desired size, shape and weight which, in the ordinary course of usage, can be placed topically on a body part (e.g., arm, leg, knee, torso, head, neck, foot as well as those parts that make-up them) for purposes of local and/or systemic administration of particular pharmaceutically active agents for a time sufficient to be effective for purposes of therapeutic activity to the body part and tissues thereof or other tissues remote from the application site in order to provide relief from the malady being suffered (e.g., pain relief though an analgesic and/or anesthetic effect) including a malady of the body part (e.g., pain and/or inflammation) to which the transdermal delivery systems, patches, vehicles and devices of the present disclosure can be directly applied for relief. After being present in contact with the body part for a time sufficient to be effective for purposes of therapeutic activity, they can be removed from the body part. Such application to the body part includes placing the transdermal delivery systems, patches, vehicles and devices in contact with the skin covering the body part.

Embodiments of the present disclosure may be delivered for local or systemic administration to a body part of a person to be treated with the embodiment, for example, a body or skin surface thereof by placing an embodiment of the present disclosure on a body part or skin surface thereof, for example, a knee, leg, back of hand, arm, lower back, upper back, shoulder and forehead, in pharmaceutically active agent-transmitting relation thereto, the pharmaceutically active agents being cannabinoid, for example, a phytocannabinoid or full spectrum hemp oil, and menthol. Alternatively, an embodiment of the present disclosure may be incorporated into a transdermal delivery system, patch, vehicle or device, such as a unit dose delivery transdermal delivery system, patch, vehicle or device.

The transdermal delivery systems, patches, vehicles and devices of the present disclosure can be of a suitable size and shape to fit against a body part so as to be applied to the skin surface thereof. The transdermal delivery systems, patches, vehicles and devices of the present disclosure include a woven or nonwoven absorbent material that is a mechanical or structural matrix in which the pharmaceutically active agent or agents along with other components (e.g., absorbent polymer, carrier solvent, surfactant, humectant, etc.) of the present disclosure are held. The absorbent material can be a layer or more than one layer in embodiments of the present disclosure and examples include gauze (e.g., cotton gauze) as well as other dressings that use synthetic and natural fibers such as nylon, rayon, abaca, hemp, flax, lyocell, pina, modal, acetate, bamboo, banana, coir, soy protein, linen, silk, polyester, polypropylene, polyethylene, polyacrylates, alginates, to name a few). Another example is a 3M Tagaderm+Pad. A suitable size for the absorbent material, for example, is illustrated in FIG. 1 which can include the shape of a square or rectangle 100 or other polygon shape (including, e.g., triangle, pentagon, hexagon, etc.) with surface areas 102 and 104 (on opposing sides) and the dimensions of sides 106, 107, 110 and 112, each ranging in length 114, 116, 118 and 120, respectively ranging from about 2.0 cm to about 8.0 cm including each surface area ranging from about 4.0 cm$^2$ to about 64.0 cm$^2$. For example, embodiments could include patches with sides 106, 107, 110 and 112, each ranging in length 114, 116, 118 and 120, respectively, that are about 2.0 cm.×about 4.0 cm (surface area about 8.0 cm$^2$).

Material thickness 122 can range from about 0.01 cm to about 0.03 cm. Volumes of the patches can range from about 0.10 ml to about 5.0 ml, in keeping with the above patch dimensions. For example, the above referenced embodiments that include patches with a surface area 8.0 cm$^2$ based on the above ranges of thickness could have volumes ranging from about 0.50 ml to about 2.0 ml.

In the embodiment of illustrated in FIG. 1 a square would have sides 105, 107, 110 and 112 approximately equal in dimensions while a rectangle would have sides 106 and 110 approximately equal in dimensions along with sides 107 and 112 approximately equal, but the dimensions of sides 106 and 110 may not always be equal to the dimension of sides 107 and 112. In other embodiments, the dimensions of any one of sides 106, 107, 110 and 112 may be equal to the dimensions of the other sides.

Figure 2A:
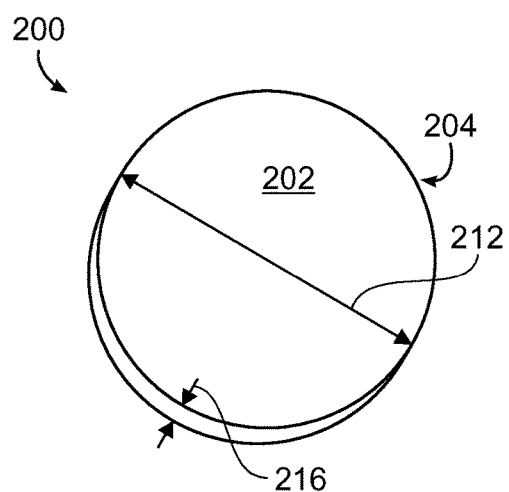
FIGS. 2A and 2B are perspective views of other embodiments of the present disclosure.
Figure 2B:
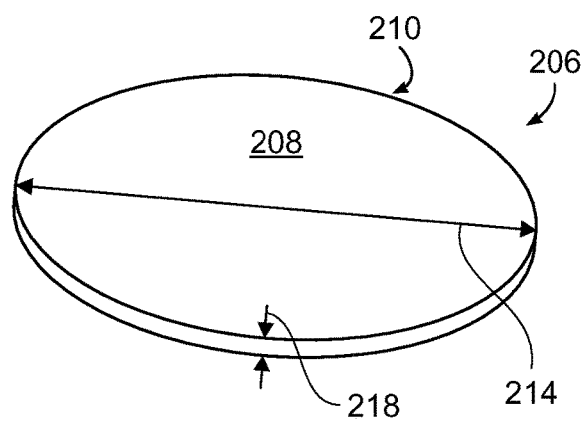

Other embodiment shapes of the absorbent material can also include a circle 200 illustrated in FIG. 2A having a generally circular shape with surface areas 202 and 204 on opposing sides thereof or an ellipse 206 illustrated in FIG. 2B and with surface areas 208 and 210 on opposing sides thereof. Diameter 212 for FIG. 2A and diameter 214 for FIG. 2B can range from about 1.0 cm to about 8.0 cm including each surface area ranging from about 0.79 $cm^2$ to about 50.27 $cm^2$.

The thickness 216 in circle 200 in FIG. 2A and thickness 218 ellipse 206 in FIG. 2B can range from about 0.01 cm to about 0.03 cm.

Non-limiting examples of injuries or other physical diseases or conditions causing pain and/or inflammation for which embodiments of the present disclosure can be used to reduce or lessen the pain and/or inflammation can include arthritis conditions (e.g., osteo, rheumatoid, psoriatic, fibromyalgia, etc.), head pain (e.g., concussion, head ache, migraine), orthopedic injuries or conditions (e.g., bone fracture or break; dislocated joint or bone; torn, stressed or strained ligament or tendon; bruising or trauma to tissue; back or spinal pain or herniated disc; tendonitis; gout, bursitis), muscles aches and pains (e.g., from stress and physical exertion) and post-surgery recovery (e.g., recovery from orthopedic surgery to repair a broken bone, back condition such as herniated disk or torn ligament, orthoscopic surgery).

Embodiments of the present disclosure include a treated absorbent material including one or more transdermally delivered therapeutic hydrophobic or hydrophilic pharmaceutically active agents, a carrier solvent, an absorbent polymer (e.g., a superabsorbent polymer) and optionally a surfactant, a humectant and a heat source material. The transdermally delivered therapeutic pharmaceutically active agents can be aqueous on non-aqueous agents.

Embodiments of the present disclosure include the treated absorbent material including cannabinoids, menthol, a carrier solvent, an absorbent polymer (e.g., a superabsorbent polymer) and optionally a surfactant, a humectant and a heat source material.

Cannabinoids are a pharmaceutically active agent and a class of chemical compounds that can be derived from plants (phytocannabinoids) or synthetically produced. Cannabinoids can have local and systemic analgesic, pain relieving, pain treating and anti-inflammatory therapeutic properties. Cannabinoids may also have other medical benefits and/or be useful in treating other medical conditions including, for example, reduction of anxiety and depression, reduction of symptoms like nausea, vomiting and pain related to cancer treatments, reduction of acne, protection of the neural system and benefits for the heart and circulatory system by the lowering of blood pressure. Cannabinoids can also have therapeutic value as a nutrient and can be included in composition and method embodiments of the present disclosure in an effective amount to perform that function.

Examples of phytocannabinoids include Cannabidiol (CBD), Cannabigerol (CBG), including, for example, CBD oil, Cannabinol (CBN) and tetrahydrocannabinol (THC), the latter being a known psychotropic compound and the first two being non-psychotropic. Cannabis and hemp plants can exhibit wide variation in the quantity and type of cannabinoids they produce. Selective breeding of the plants can be used to control the genetics of plants and modify the cannabinoids produced by the plant. For example, there are strains that are used as fiber (commonly called hemp) and, as a result, have been bred such that they are low in psychoactive chemicals like THC. Such strains (e.g., hemp) used in medicine are, for example, often bred for high CBD content and have minimal levels of THC (less than 0.3%). Some embodiments of the present disclosure include a cannabinoid component with less than 0.3% THC. Examples of topical, transdermal and/or pharmaceutically effective cannabinoids include CBD (for example, full spectrum hemp oil). Cannabinoid, including, for example, phytocannabinoids including CBD, can be in an amount of about 0.10 wt % to about 20.00 wt % (based on 25% CBD conc. in CBD or hemp oil). CBD can be in an amount of 0.025 wt % to about 5.00 wt %. Full spectrum CBD or hemp oil can be in an amount of about 0.10 wt % to about 20.00 wt % (based on 25% CBD conc. in the CBD or hemp oil). Unit dosage formulations of the embodiments of the present disclosure can include cannabinoid, for example, a phytocannabinoid (including for example, CBD) in the amount of about 5.0 mg. to about 5000.00 mg. (based on 25% CBD conc. in the CBD or hemp oil). Unit dosage formulations of the embodiments of the present disclosure can include CBD in the amount of about 1.250 mg. to about 1250.00 mg. Unit doses of full spectrum CBD or hemp oil can include an amount of about 5.0 mg. to about 5000.00 mg. (based on 25% CBD conc. in the CBD or hemp oil). Unit dosage formulations of the embodiments of the present disclosure can include cannabinoid, for example, a phytocannabinoid (including for example, CBD) or full spectrum hemp oil in the amount of about 5.0 mg/ml. to about 1000.00 mg/ml. (based on 25% CBD conc. in the hemp oil). Unit dosage formulations of the embodiments of the present disclosure can include CBD in the amount of about 1.25 mg/ml. to about 250.00 mg/ml. Unit dosage formulations of the embodiments of the present disclosure can include full spectrum CBD oil in an amount of about 5.0 mg/ml. to about 1000.00 mg/ml (based on 25% CBD conc. in the CBD oil).

Unit dosage formulations of the embodiments of the present disclosure can include cannabinoid, for example, a phytocannabinoid (including for example, CBD) in the amount per unit of surface area (e.g., surface areas 102 and 104 in FIG. 1, in FIG. 2A with surface areas 202 and 204 and in FIG. 2B and with surface areas 208 and 210) of about 5.0 mg/$cm^2$ to about 5000.00 mg/$cm^2$. Unit dosage formulations of the embodiments of the present disclosure can include CBD in the amount of about 1.25 mg/$cm^2$ to about 250 mg/$cm^2$. Unit dosage formulations of the embodiments of the present disclosure can include full spectrum CBD or hemp oil in an amount of about 5.0 mg/$cm^2$ to about 5000 mg/$cm^2$. An effective amount of cannabinoid includes an analgesic, pain relieving, pain treating or anti-inflammatory amount of cannabinoid.

Cannabinoids, for example, CBD can have a local and/or a systemic effect and may reduce pain imparting and regulating the endocannabinoid (neurotransmitter of the nervous system) receptor activity. The subsequent body functions that may be regulated include pain, sleep, appetite and immune system response (through, at least, in part, by reducing inflammation).

For the purpose of the present disclosure, the word "cannabinoid" refers to one or more cannabinoids or cannabinoid compounds or oils or extracts from plants (for example, hemp including hemp oil and full spectrum CBD or full spectrum hemp oil) that include one or a plurality of phytocannabinoids.

Full spectrum hemp oil is oil derived from the entire plant except the flower (which contains THC) and can have over 85 phytocannabinoids which can have a positive synergistic effect as compared to compositions having fewer cannabinoids. There may also be benefits to other components of it (e.g., terpenes). Such benefits and effect may include faster penetration and/or permeation of the therapeutic components thereof. Full spectrum hemp oil can include full spectrum hemp oil that has been purified to include less than the below stated amounts of one or more of the following impurities:

Aflatoxins B1, 82, G1, G2 (fats, oils, lecithin, egg powder): <0.1 µg/kg of each of Aflatoxin B1, Aflatoxin B2, Aflatoxin GI and Aflatoxin G2, Sum of all positive Aflatoxins <0.4 µg/kg.

GlyphosateIAMPAiGlufosinate: <0.1 mg/kg of each of Glufosinate, Glyphosate and Aminomethylphosphonic acid (AMPA)

Mercury: <0.02 mg/kg

Arsenic: <0.03 mg/kg

Cadmium: <0.01 mg/kg

Lead: <0.05 mg/kg.

Embodiments of the present disclosure may also optionally include an effective amount of THC. Unit dosage formulations of the embodiments of the present disclosure can include THC in the amount of about 0.1 mg. to about 10 mg., about 1 mg. to about 10 mg., about 4 mg. to about 6 mg. about 5 mg. In addition to the other benefits that can be provided by other cannabinoids, THC may relieve stress and be a sleeping aid.

Menthol is a pharmaceutically active agent and an organic compound that can be made synthetically or obtained from mint oils such as corn mint and peppermint. Medicinally, it been found that menthol can have anesthetic (e.g., local) by, for example, blocking nerve signal transmission) and counterirritant properties as well as anti-inflammatory properties (e.g., systemic and local) as well as a cooling effect when administered topically to a patient. Furthermore, menthol is a vasodilator that can accelerate the transport of other pharmaceutically active agents in the circulatory system. In general, the action of local anesthetics can restrict to the site of application and rapidly reverses upon diffusion from the site of action in the nerve. Local anesthetics can also serve an important function in providing peripheral pain relief. Topical administration of pain-relieving anesthetics can provide important advantages over systemic or local, non-topical administration. Menthol can be in an amount of about 0.05 wt % to about 20.00 wt. Unit dosage formulations of the embodiments of the present disclosure can include menthol in the amount of about 0.0025) mg. to about 1000.00 mg. Unit dosage formulations of the embodiments of the present disclosure can include menthol in the amount of about 0.0025) mg/ml. to about 200 mg/ml. Unit dosage formulations of the embodiments of the present disclosure can include menthol in the amount per unit of surface area (e.g., surface areas 102 and 104 in FIG. 1, in FIG. 2A with surface areas 202 and 204 and in FIG. 2B and with surface areas 208 and 210) of about 0.0005 mg/cm$^2$ to about 1000.00) mg/cm$^2$. An effective amount of menthol includes an anesthetic, pain reducing (e.g., analgesic) or anti-inflammatory effective amount of menthol.

Menthol may be stabilized using methods know in the art, such as, for example, mixing it with about 0.1 wt % to about 10 wt %, about 0.5 wt % to about 5 wt % of a surfactant including edible nonionic surfactants and ionic surfactants, such as, for example, sucrose fatty acid ester, polysorbate (e.g., polysorbate 80), hydrogenated castor oil (e.g., polyoxyethylene hydrogenated castor oil), cocamidopropyl betaine, cyclodextrins, adsorbents, encapsulations, nanoemulsions etc.

The aspects of the present disclosure also relate to embodiments including compositions, methods of making and methods of using included herein which also comprise the menthol component included in embodiments of the present disclosure in a stabilized or more stable menthol composition as well as methods of making and using them including a pre-formed mixture of (a) menthol and (b) at least one menthol stabilizer compound including undecylenic acid methyl ester or undecylenic acid or a salt (preferably a pharmaceutically acceptable salt) thereof where the menthol in the stabilized menthol compositions is less susceptible to volatizing into a gas and remains in a form that can be administered in a composition in an amount closer to the amount originally included in the composition when formulated with less menthol volatizing away (i.e., lowering the rate of volatilization of the menthol from what it would be for menthol alone) from the original concentration and, thus, lowering the original concentration and diminishing the amount of the menthol originally added. The pre-mixing of menthol and the menthol stabilizer compound and the resulting premixture is formed before it is added to any of the other components of the composition.

Undecylenic acid salts, including pharmaceutically acceptable salts may include, for example, inorganic acid addition, hydrochloride salts, sulfate and phosphate salts; and organic acid addition salts, such as alkyl sulfonate, arylsulfonate, acetate, maleate, fumarate, tartrate, citrate and lactate and metal salts including alkali metal salts, such as lithium salt, sodium salt and potassium salt and alkaline earth metal salts, such as magnesium salt and calcium salt, strontium salt, aluminum salt and zinc salt, and other multivalent salts such as for example, zirconium, iron, copper, silver, bismuth etc. Additionally, primary secondary, and tertiary amine salts, organic and inorganic, mono and polyamines compounds could be utilized. Examples include compounds such as urea, and amino acids such as lysine, histidine, arginine etc., could be utilized.

The stabilized or more stable menthol compositions can made by mixing together (a) menthol and (b) a menthol stabilizer compound in a ratio of (a) about 1 molar part menthol to (b) the amount of one or more than one of the menthol stabilizer compounds (undecylenic acid methyl ester, undecylenic acid or a salt (preferably a pharmaceutically acceptable salt) of undecylenic acid, including mixtures thereof) of from about 0.005 molar part to about 1.00 molar part, about 0.010 molar part to about 0.750 molar part, about 0.020 molar part to about 0.50 molar part, about 0.050 molar part to about 0.250 molar part, or about 0.10 molar part. It is believed that the menthol stabilizer compounds (e.g., undecylenic acid methyl ester and others included herein) and menthol may associate to form a menthol analog where the menthol analog's vapor pressure becomes lower than menthol itself. As a result of having a lower vapor pressure, the menthol component of the menthol analog volatizes as a lower rate than menthol by itself.

One possible explanation for the stabilization of menthol by the compound of formula (I) may be that the menthol associates with the alkenyl side chain of the menthol stabilizer compounds may provide a molecular attraction connecting the menthol stabilizer compounds and a menthol molecule, such that more than one menthol molecule may associate with a molecule of one of the menthol stabilizer compounds.

The stabilized or more stable menthol compositions including menthol and at least one of the menthol stabilizer compounds (e.g., undecylenic acid methyl ester and others included herein) can also be made first by dissolving menthol in a pharmaceutically acceptable suitable solvent such as, for example, as a low, medium, or long chain triglyceride. Examples of such solvents are coconut oil, olive oil, palm oil, hemp oil and castor oil. Still other acceptable solvents, such as alcohols, ethers and polyalcohols, for example, propylene glycol, butylene glycol, and polyethylene glycols (PEGs) can also be used. The desired amount of at least one of the menthol stabilizer compounds disclosed herein (e.g., undecylenic acid methyl ester and others disclosed herein) is then added to that mixture. Such compositions that include menthol, solvent and one or more than one of the menthol stabilizer compounds included herein may be made where the mixture of the these ingredients includes a molar ratio of about one molar part menthol to a range of from about 0.0050 molar part to about 1.00 molar part, about 0.010 molar part to about 0.750 molar part, about 0.020 molar part to about 0.50 molar part, about 0.050 molar part to about 0.250 molar part, or about 0.10 molar part of at least one of the menthol stabilizer compounds (i.e., one of the menthol stabilizer compounds or a mixture of more than one of the menthol stabilizer compounds) included herein, preferably a molar ratio of about one molar part menthol to at most about 0.50 molar part, at most about 0.250 molar part or at most about 0.10 molar part of one or more than one of the menthol stabilizer compounds included herein. Such mixtures of menthol, solvent and menthol stabilizer compounds may be used when smaller amounts of menthol need to be stabilized (where the amount of menthol stabilizer compound to be mixed with the menthol is so small that there isn't enough of it to dissolve the menthol).

Both stabilized or more stable menthol compositions (i.e., where the menthol is first dissolved in a solvent then dissolved in a menthol stabilizer compound included herein or where the menthol is directly dissolved in a menthol stabilizer compound included herein) can be used in orally administered and non-orally administered compositions (e.g., non-orally topically administered compositions (e.g., place on the skin or other external tissues)). However, the menthol stabilizer compounds can have a bitter taste. The dissolving of the menthol in solvent prior to the addition of at least one of the menthol stabilizer compounds included herein is preferably used in menthol containing therapeutic compositions to be administered orally because by first dissolving the menthol in a suitable solvent, less of the menthol stabilizer compounds may be used, thus lessening the bitter taste of the menthol stabilized composition and the final product in which it is included that is imparted by the menthol stabilizer compound.

The carrier solvent is used to form a solution matrix in which the other ingredients in the absorbent material and specifically in the absorbent polymer in the absorbent material are held. Examples of carrier solvents can include coconut oil, medium chain triglycerides, olive oil, castor oil, canola oil, triacetin, corn oil, petrolatum, mineral oil, shea butter, avocado oil, squalene. Essential oils such as anise oil, bay oil, sage oil, cranberry and fennel seed oil, lemongrass oil, tea tree oil, etc. The carrier solvent can be in an amount of about 20.00 wt % to about 90.00 wt %.

The absorbent polymer (e.g., a superabsorbent polymer) can include suitable biocompatible polymers that act as gelling, thickening and/or stabilizing agents can include for example of, including pharmaceutically acceptable biocompatible polymers, can include gelatin, agar, sodium carboxymethylcellulose, pectin, sodium alginate, sodium/calcium alginate, polylactic acid, chitosan, carageenan, xanthan, gellan, polyaspartic acid, polyglutamic acid, hyaluronic acid or salts or derivatives thereof, polyacrylates, polyacrylamides, methylvinylether maleic acid/anhydride, PVP, polyethylene oxide, etc. A preferred biocompatible polymer is sodium carboxymethylcellulose, preferably crosslinked, such as crosscarmellose sodium, sodium starch glycolate, soy polysaccharides, PVPP, etc. The absorbent polymer, such as, for example, crosscarmellose sodium, can be in an amount of about 0.01 wt % to about 5.00 wt %. Some of the absorbent polymers may also stabilize or make more stable the menthol component of embodiments of the present disclosure. The absorbent polymer may contain less than 0.5% lower residual water, less than 0.3% lower residual water, less than 0.1% lower residual water.

Embodiments of the present disclosure can also optionally include a humectant, the inclusion of which is preferable because the humectant can act as a moisturizer to keep the skin moist and keeping it from drying out. The humectant can include polyalcohols (e.g., pharmaceutically acceptable biocompatible polyalcohols), hyaluronic acid, sorbitol, honey, allantoin, etc. Pharmaceutically acceptable biocompatible polyalcohols, can include alcohols containing 2 to 10 carbon atoms and 2 to 7 hydroxyl groups including, for example, ethylene glycol, propylene glycol, butylene glycol, glycerin, glycerin betaine, erythrit (meso-1,2,3,4-Butantetrol), sorbit, mannit, methylglucoside, diglycerine, triglycerine and/or pentaerythrit as well as sodium lactate. Humectants, such as for example, glycerin can be in an amount of from about 0.50 wt % to about 10.00 wt %. The humectant may contain less than 0.5% lower residual water, less than 0.3% lower residual water, less than 0.1% lower residual water.

Embodiments of the present disclosure can also optionally include a surfactant. The surfactant can include anionic surfactants, such as, for example alkylbenzene sulfonates, ammonium lauryl sulfates, ammonium oerfluoronanoate, sodium and potassium sulfate derivatives, phospholipids, cocamidopropylbetaine, sodium docusates, perfluoro acid derivatives, sodium cocoate, etc. and nonionic surfactants, such as, for example, polysorbate 80, hydrogenated Castor oil, alkyl polyglucosides, cetyl alcohol, Cocamide DEA/MEA, glucoside derivatives nonoxynols, poloxamers, sorbitans, PEGs, glycerol monostearates, etc. Surfactants, such as for example, polysorbate 80 can be in an amount of about 0.10 wt % to about 3.00 wt.

Embodiments of the present disclosure can also optionally a heat source material, such as a material that generates heat (e.g., through an exothermic reaction) upon contact with water. The heat source material can be, for example, zeolite, sodium acetate, iron powder, etc.). The heat source material, such as for example, zeolite can be in an amount of about 1.00 wt % to about 20.00 wt.

Figure 3A:
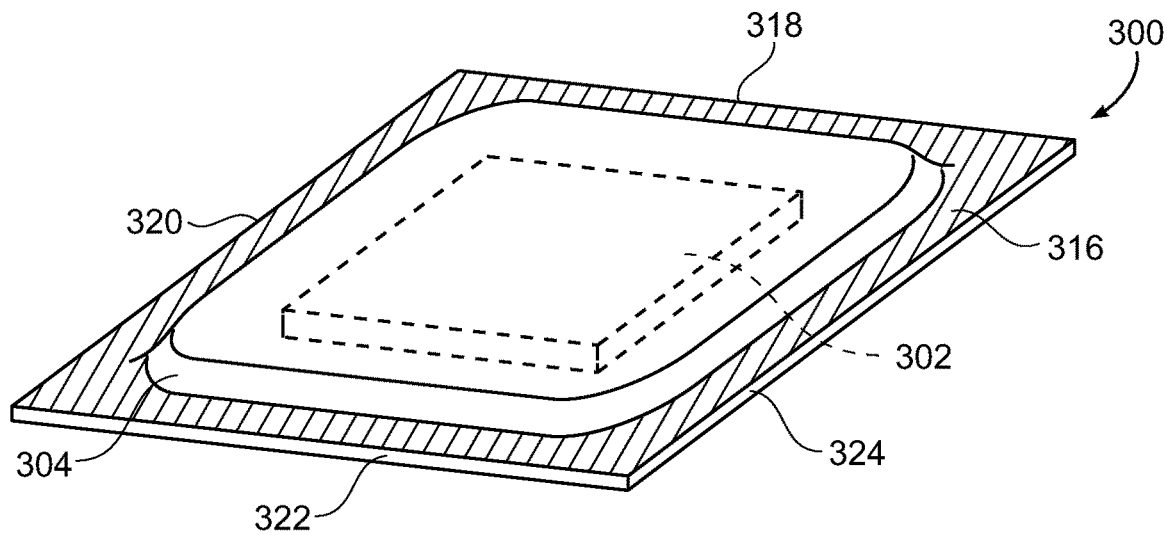
FIGS. 3A, 3B and 3C are a perspective and cross-sectional view of exemplary embodiments of the present disclosure.
Figure 3B:
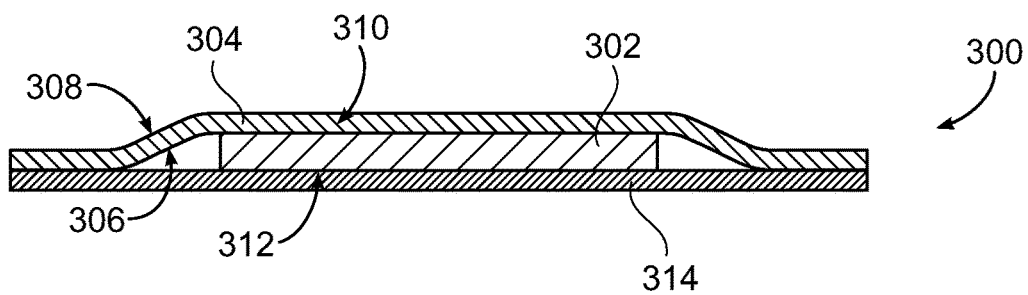

Embodiments of the present disclosure also includes the treated absorbent material of the present disclosure (for example, in the shapes and dimensions illustrated in FIGS. 1, 2A and 2B) and an adhesive backing that keeps the treated absorbent material that keeps a substantial amount, if not all, of the surface area of the treated absorbent material (e.g., surface areas 102 or 104 in FIG. 1, in FIG. 2A surface areas 202 or 204 and in FIG. 2B surface areas 208 or 210) in contact with the skin of the user to hold the treated absorbent material against the skin of the user. An exemplary embodiment of the present disclosure is shown in FIGS. 3A and 3B including a transdermal delivery system, patch, vehicle or device 300 which includes treated absorbent material layer 302 and backing material 304. The backing material 304 can be a plastic cover that is substantially resistant to moisture transport therethrough, such as, for example, PVdC—polyvinylidene chloride. The backing material 304 can have an adhesive side 306 and a side 308 that is adhesive free. The adhesive side 306 can be, but need not be in contact with side 310 of treated absorbent material with side 312 of the treated absorbent material positioned to be against the skin 314 of the user upon application of the transdermal delivery system, patch, vehicle or device 300. At least a portion of adhesive side 306 of backing material 304 is in contact with skin 314 to adhere the transdermal delivery system, patch, vehicle or device 300 to and hold in position the treated absorbent material layer 302 against or in substantial contact with skin 314. As an alternative embodiment, backing material 304 can include adhesive material limited to, but substantially covering the peripheral area 316 adjacent the edge 318, 320, 322 and 324 thereof as shown in FIG. 3A.

The adhesive (preferably a topically or dermally acceptable adhesive) for the adhesive portion of the backing material 304 or other embodiments of the present disclosure can be a pressure sensitive topically acceptable adhesive, such as, for example, acrylics, butyl rubber, ethylene-vinyl acetate (EVA), natural rubber, nitriles, silicone rubbers, styrene block copolymers (SBC), styrene-butadiene-styrene (SBS), styrene-ethylene/butylene-styrene (SEBS), styrene-ethylene/propylene (SEP), styrene-isoprene-styrene (SIS), as well as hydrophilic pressure sensitive adhesives (PSA) such as for example polyvinylpyrrolidone-polyethylene glycol copolymers (PVP-PEG), maleic anhydride vinyl ether-methyl- and amine-terminated polyethylene glycol copolymers (MVE/MA-PEG), and polyethylene oxide-polyethylene glycol copolymers (PEO-PEG).

Upon application of the transdermal delivery system, patch, vehicle or device embodiments of the present disclosure, including, for example, side 312 being placed against the skin 314 of the user, the carrier solvent (e.g., coconut oil) melts due to the heat of the skin. An embodiment of the present disclosure can also include as part of the absorbent material a surfactant that is released and associates with the skin oils in order to break them up and prepares and conditions the skin and make it easier to wet the skin. An alternative to including a solvent as part of the absorbent material would be to separately clean the area of skin on which the transdermal delivery system, patch, vehicle or device embodiments of the present disclosure is to be placed prior to applying it to the skin. Such cleaning of the area could be done using a surfactant (e.g., as included in embodiments of the present disclosure) or other acceptable cleaning compositions to break them up and prepares and conditions the skin and make it easier to wet the skin.

After application of an embodiment of the present disclosure (where the skin in cleaned prior to application of the embodiment that does not include surfactant or the embodiment including surfactant is applied after the skin), moisture from the skin is wicked into the treated absorbent material and the hydrophilic components (e.g., absorbent polymer and humectant (such as glycerin, if present)) and thereby displaces and drives the other components (for example, oil components or hydrophobic components; e.g., cannabinoids and menthol) out of the treated absorbent material and toward the skin so that they are absorbed through the pores essentially via osmosis but because there is heat radiated from the skin plus the surfactant plus coconut oil, the osmosis is enhanced. The warmth of the skin can also contribute to melting the carrier solvent prior to moisture from the skin wicking into the treated absorbent material. In embodiments where the heat source is present, the moisture from the skin also reacts with the heat source (e.g., zeolite), thereby causing an exothermic reaction and generating additional heat that can contribute to melting the carrier solvent and warms the skin to open the pores of the skin, thereby making the skin more receptive and accelerating the administration and penetration of pharmaceutically active agents, for example, hydrophobic components (e.g., cannabinoids and menthol).

In a further embodiment, a kit is disclosed. One example of such a kit is a kit including one or more of the embodiments of the present disclosure separately packaged and instructions for use.

Figure 4A:
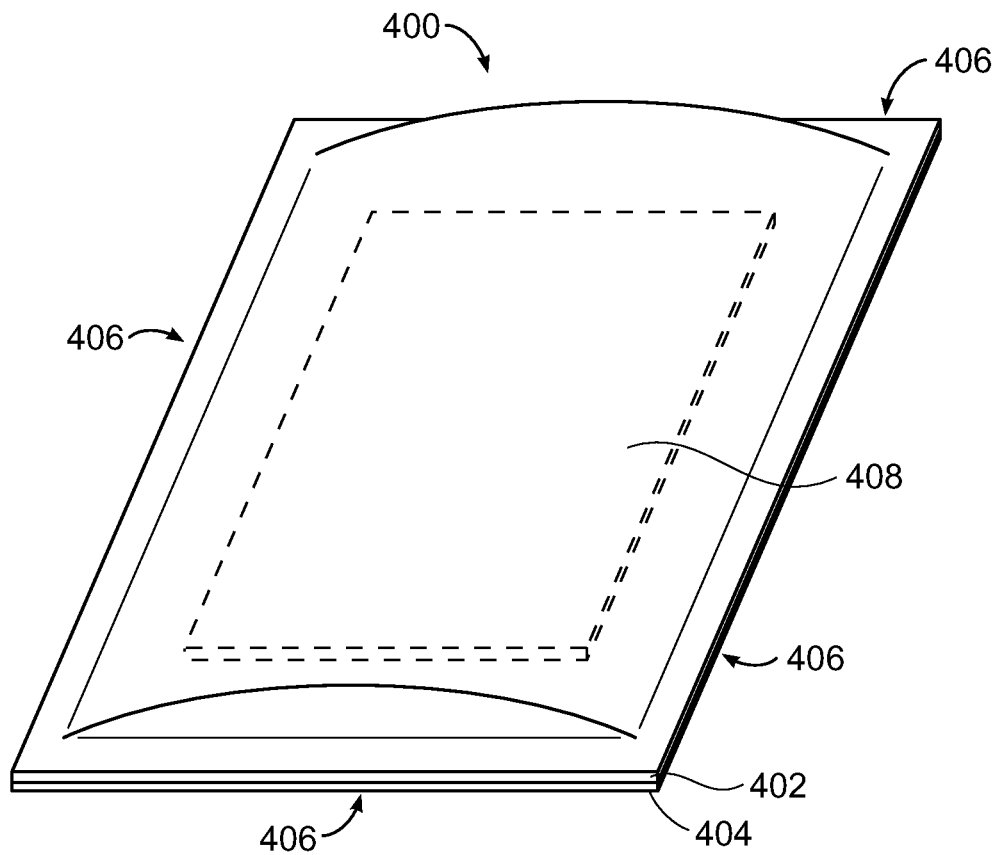
FIGS. 4A and 4B illustrate perspective and cross-sectional views of an exemplary packaging embodiment of the present disclosure.
Figure 4B:
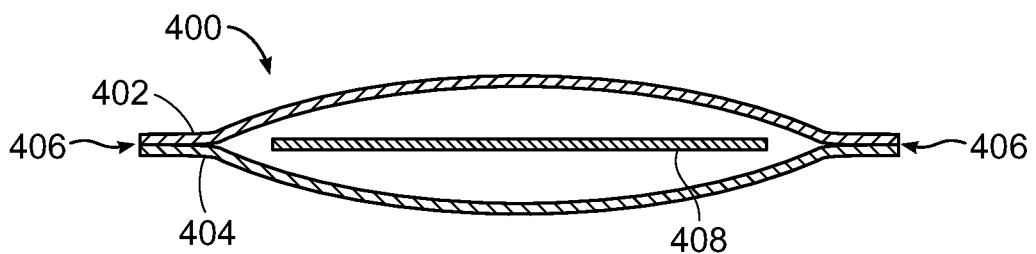

An example of such a kit is a sealed water-proof package containing an embodiment of the present disclosure. Another aspect of the present disclosure is a water-proof package designed to contain of the composition or patch embodiments of the present disclosure and to keep a substantial amount of the moisture (i.e., water) in the embodiment. One package embodiment is illustrated in FIGS. 4A and 4B and can include foil enclosure 400 with side sections 402 and 404 that are sealed together along a common peripheral edge 406. Inside the enclosure 400 is an internal void in which a transdermal delivery system, patch, vehicle or device embodiment of the present disclosure 408 is positioned.

Figure 5A:
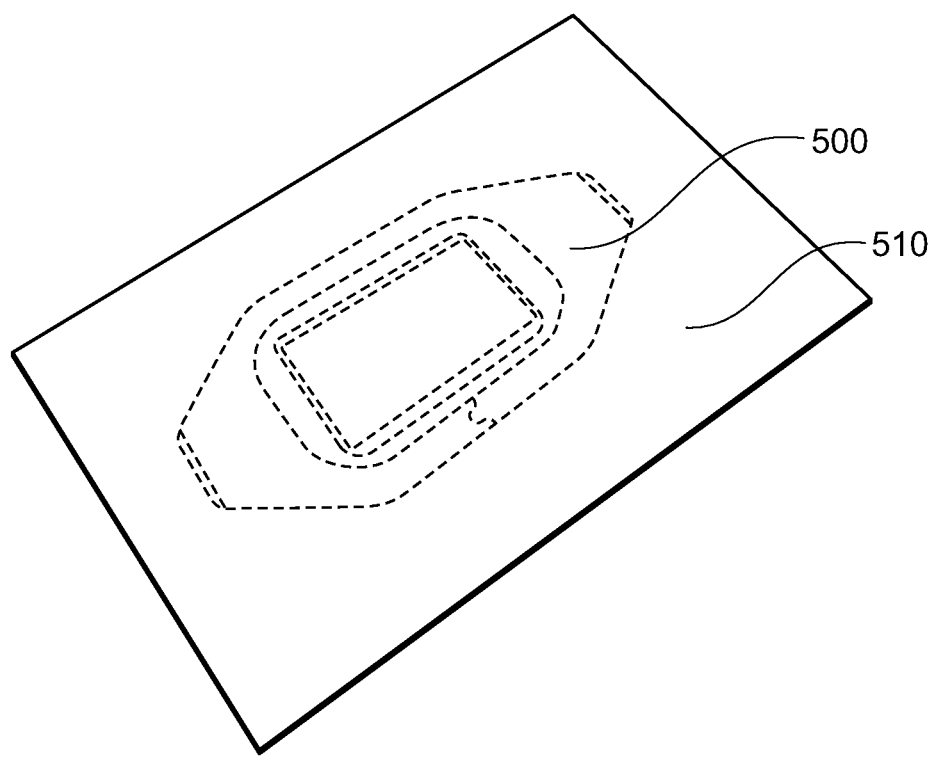
FIGS. 5A to 5F illustrate an embodiment and application thereof and a cross-section of an embodiment of the present disclosure.
Figure 5B:
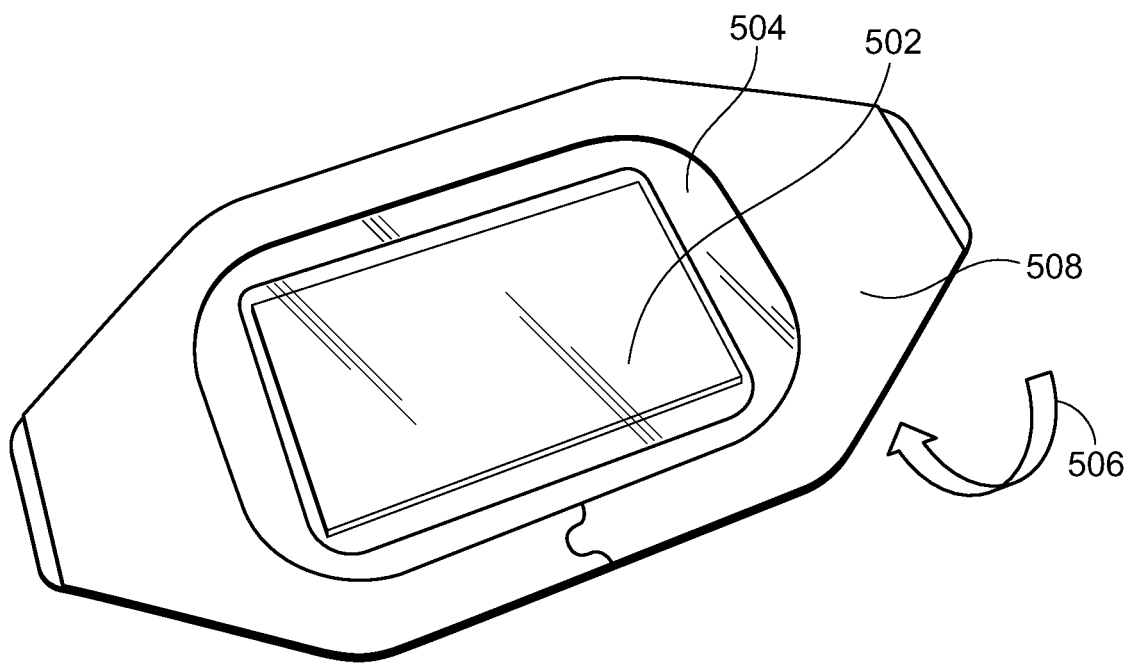
Figure 5C:
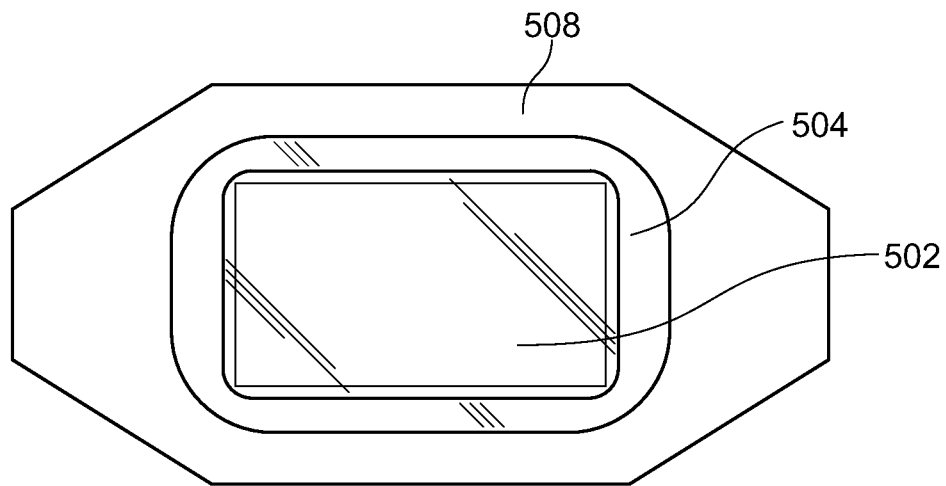
Figure 5D:
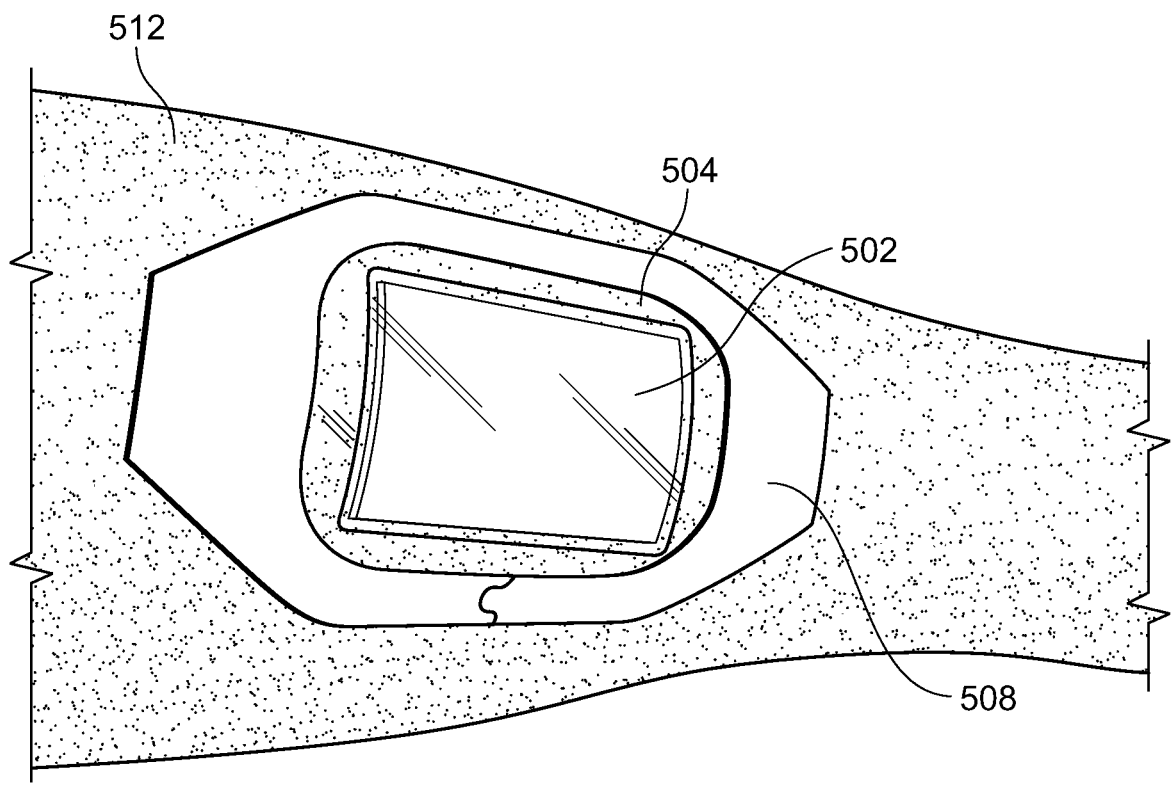
Figure 5E:
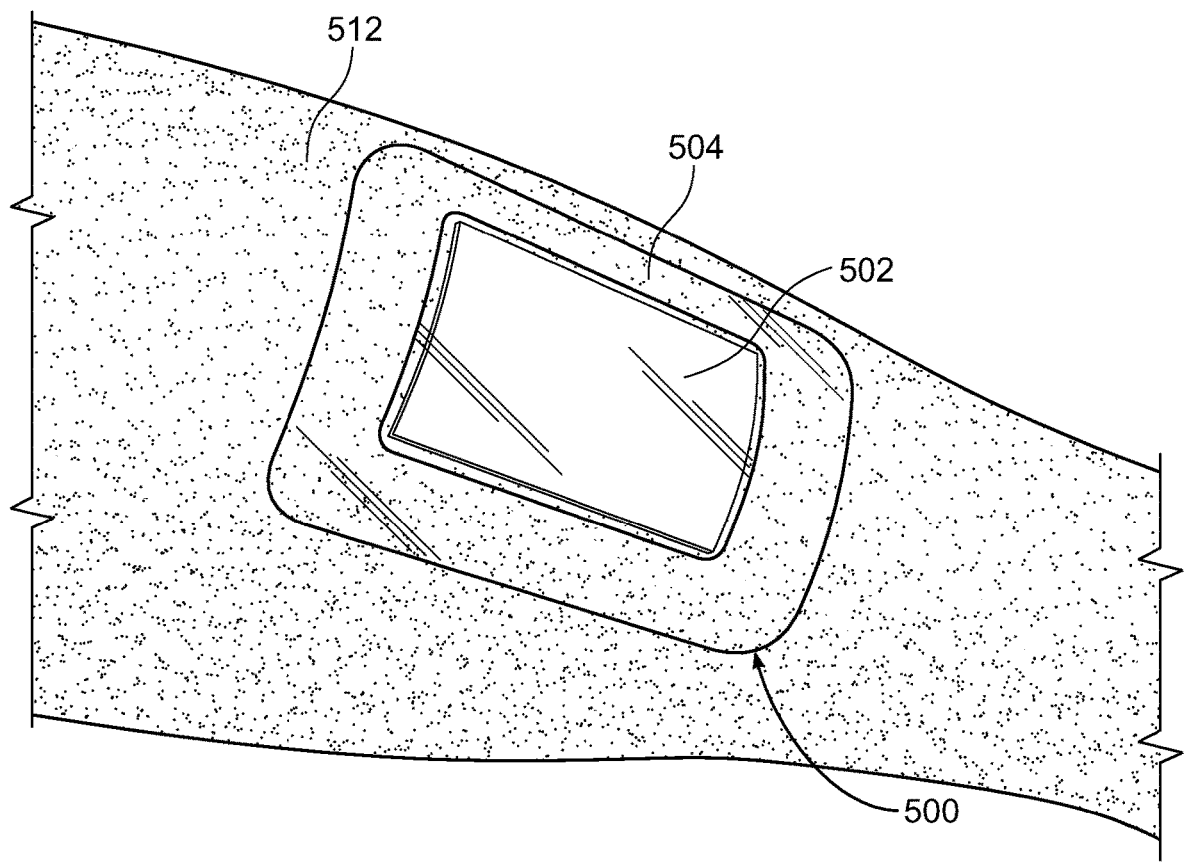
Figure 5F:
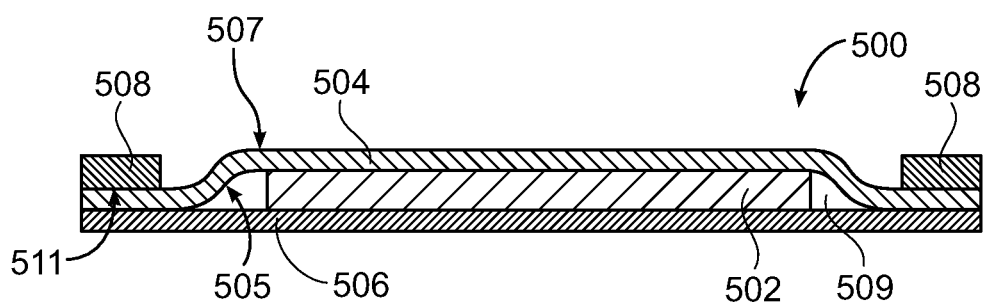

Packaging and application of embodiments of the present disclosure are shown in FIGS. 5A-5F that includes a transdermal delivery system, patch, vehicle or device 500 embodiment of the present disclosure which includes treated absorbent material layer 502 and backing material 504 including an adhesive side 505, a bottom release layer 506 and a top release layer 508 that are packaged in a sealed envelope 510, for example, a package embodiment of the present disclosure, that is made of material that is substantially resistant to moisture transport therethrough, such as, for example, a laminate film. After being removed from the sealed envelope 510, the bottom release layer 506 is removed and the adhesive side 505 of the backing material 504, as shown in FIG. 5D, is placed in contact with user skin layer 512 with some pressure applied to ensure the adhesion thereto of the backing material surrounding the treated absorbent material layer 502. Thereafter, the top release layer 508 can be removed from the transdermal delivery system, patch, vehicle or device 500. The top release 508 includes an adhesive side 511 that includes a pressure sensitive adhesive similar to those of embodiments of the present disclosure and is in contact with the adhesive free side 507 of the backing layer 504 and may completely or substantially cover the surface of the adhesive free side 507 or an area of the adhesive free side 507 adjacent the outer periphery of backing layer 504 as shown in the embodiment including peripheral area FIG. 3A and not covering or substantially not covering cavity 509 in which treated absorbent material layer 502 is positioned. The bottom release layer can be in contact with both the backing layer 504 and the treated absorbent material layer 502 as shown in FIG. 5F or just the backing material 504.

The terms "treating" and "effective amount", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neoadjuvant treatment of a subject.

All of the embodiments included here are with the proviso that the sum of ingredients in the exemplary compositions does not exceed 100%.

Other embodiments of the present disclosure include a method of relieving pain and/or inflammation by topically administering and placed topically to a body part (e.g., arm, leg, knee, torso, head, neck, foot as well as those parts that make-up them), of a mammal (e.g., a human patient or veterinary patient) in need of such treatment at least one of the compositions disclosed herein. Still other embodiments of the present disclosure include a method of relieving bodily pain (local and/or systemic) by topically administering to placed topically on a body part (e.g., arm, leg, knee, torso, head, neck, foot as well as those parts that make-up them), of a mammal (e.g., a human patient or veterinary patient) in need of such treatment at least one of the compositions disclosed herein. Still other embodiments of the present disclosure include a method of relieving pain and/or inflammation (local and/or systemic) by administering to a body part, for example, placed topically on an arm, leg, knee, torso, head, neck, foot as well as those parts that make-up them, of a mammal (e.g., a human patient or veterinary patient) in need of such treatment at least one of the compositions disclosed herein. Still other embodiments of the present disclosure include a method of relieving bodily pain and/or inflammation (local and/or systemic) by topically administering to placed topically on a body part (e.g., arm, leg, knee, torso, head, neck, foot as well as those parts that make-up them), of a mammal (e.g., a human patient or veterinary patient) in need of such treatment at least one of the compositions disclosed herein by placing the composition topically on a body part (e.g., arm, leg, knee, torso, head, neck, foot as well as those parts that make-up them).

Figure 6C:
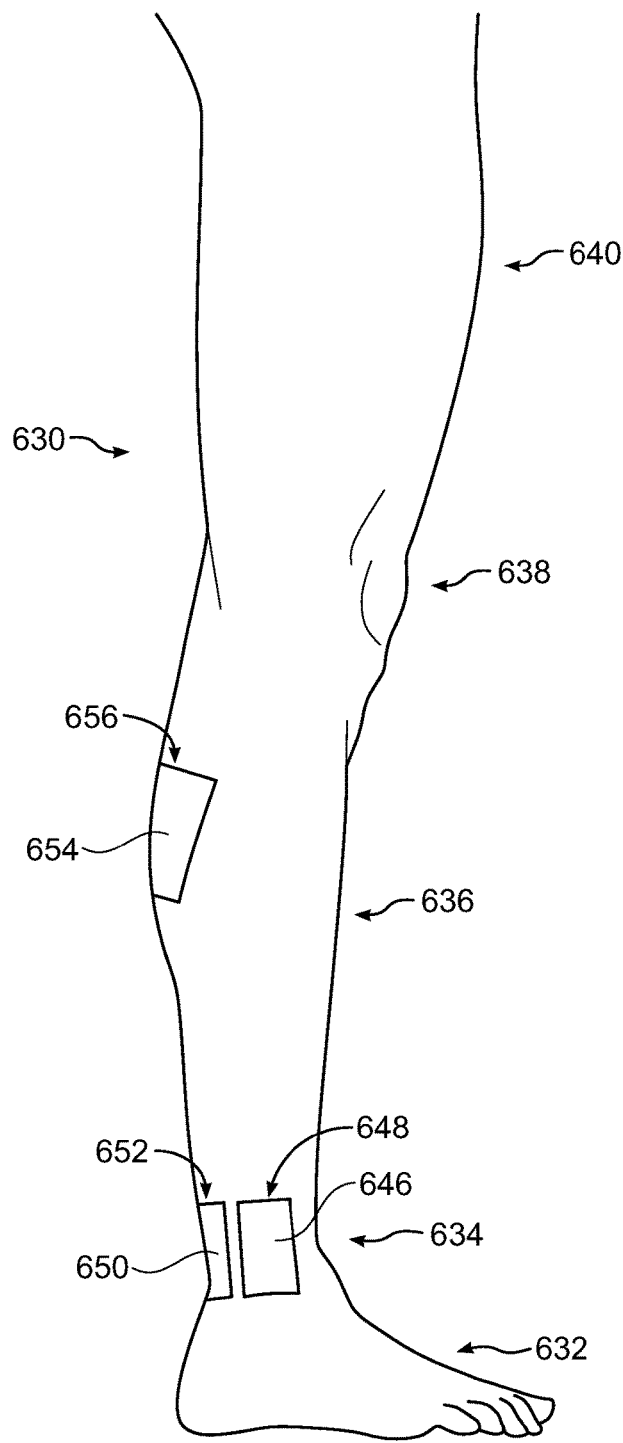

Embodiments of the present disclosure are intended to be placed on the skin surface of a body part or body parts or portions thereof where a person is experiencing pain and/or inflammation resulting from, for example, injury or other physical diseases, stresses or conditions. Non-limiting exemplary embodiments showing possible placement are illustrated in FIGS. 6A to 6F. FIGS. 6A and 6B show a top view and side view, respectively, of an arm 600 including a hand 602, wrist 604, forearm 606, elbow area 607 and upper arm 608. One of the embodiments of the present disclosure 610 can be positioned against the hand 602 at 612. An alternative is an embodiment of the present disclosure 614 can be positioned against the wrist 604 at 616. An alternative is an embodiment of the present disclosure 618 can be positioned against the forearm 606 at 620. An alternative is an embodiment of the present disclosure 619 can be positioned against the lower part of the forearm 606 at 621. An alternative is an embodiment of the present disclosure 622 can be positioned against the elbow area 607 at 624. An alternative is an embodiment of the present disclosure 626 can be positioned against the upper arm 608 at 628.

Figure 6D:
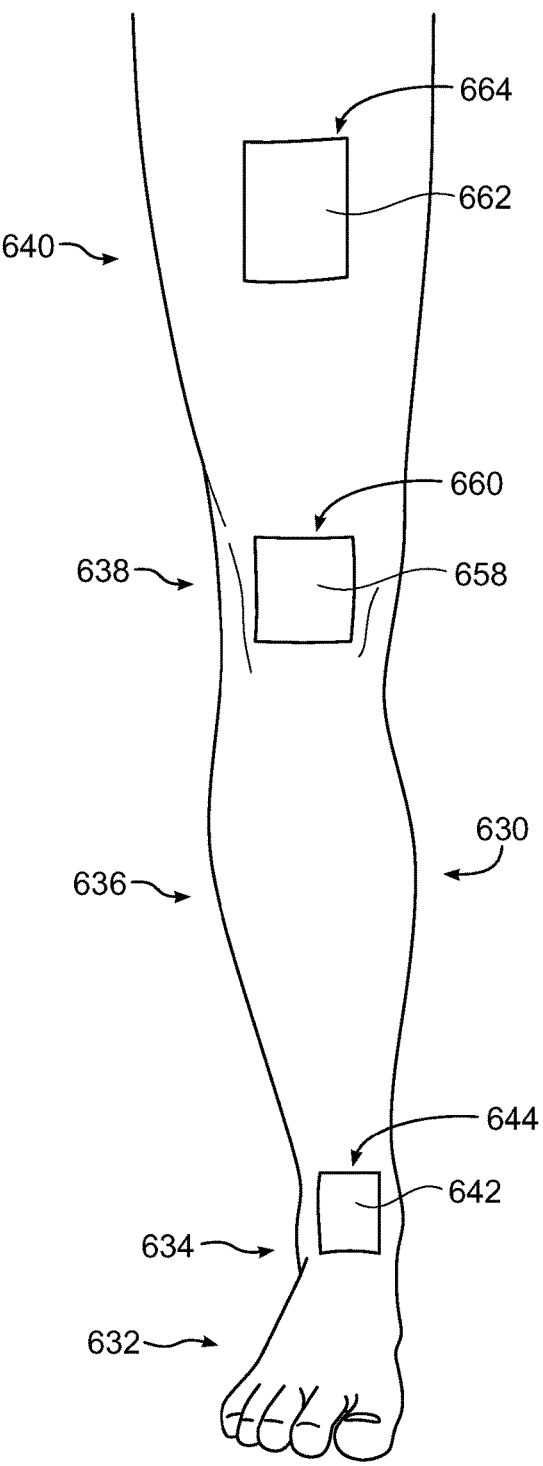

FIGS. 6C and 6D show a side view and front view, respectively, of a leg 630 including a foot 632, ankle area 634, calf 636, knee area 638 and upper leg 640. One of the embodiments of the present disclosure 642 can be positioned against the front of the ankle area 634 at 644. An alternative is an embodiment of the present disclosure 646 can be positioned against the side of the ankle area 634 at 648. An alternative is an embodiment of the present disclosure 650 can be positioned against the back of the ankle area 634 (e.g., against the Achilles tendon) at 652. An alternative is an embodiment of the present disclosure 654 can be positioned against the side of the back of the calf 636 at 656. An alternative is an embodiment of the present disclosure 658 can be positioned against the knee area 638 at 660. An alternative is an embodiment of the present disclosure 662 can be positioned against the front of the upper leg 640 at 664.

Figure 6E:
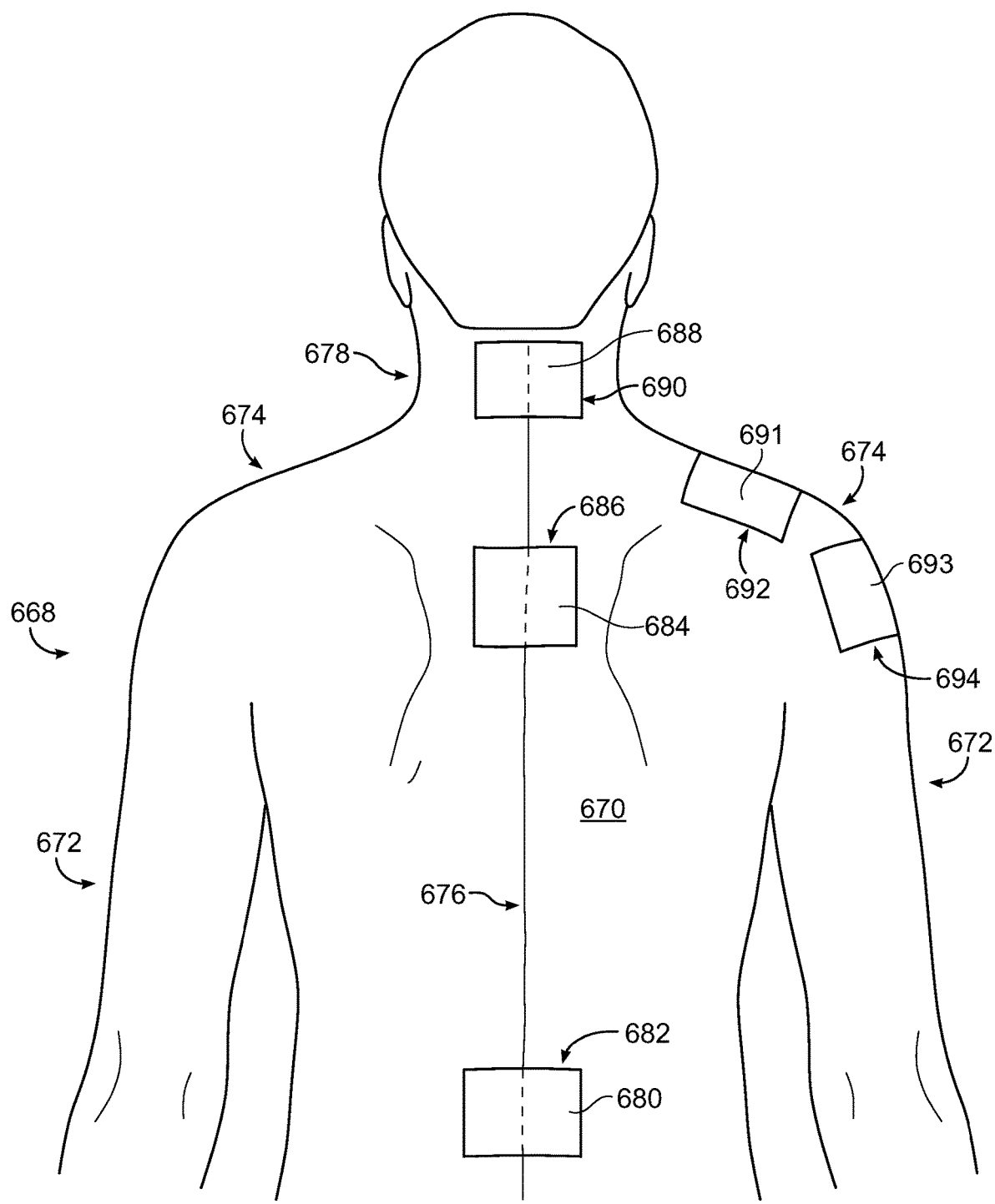

FIG. 6E shows a rear view of an upper torso 668 including back 670, arms 672, shoulder area 674, spinal/backbone area 676 and neck 678. One of the embodiments of the present disclosure 680 can be positioned against the lower region of the back 670 adjacent the spinal/backbone area 676 at 682. An alternative is an embodiment of the present disclosure 684 can be positioned against the upper region of the back 670 adjacent the spinal/backbone area 676 at 686. An alternative is an embodiment of the present disclosure 688 can be positioned against the back of the neck 678 (e.g., against the spinal/backbone area 676) at 690. An alternative is an embodiment of the present disclosure 691 can be positioned against the upper area of the shoulder area 674 at 692. An alternative is an embodiment of the present disclosure 693 can be positioned against the lower area of the shoulder area 674 at 694.

Figure 6F:
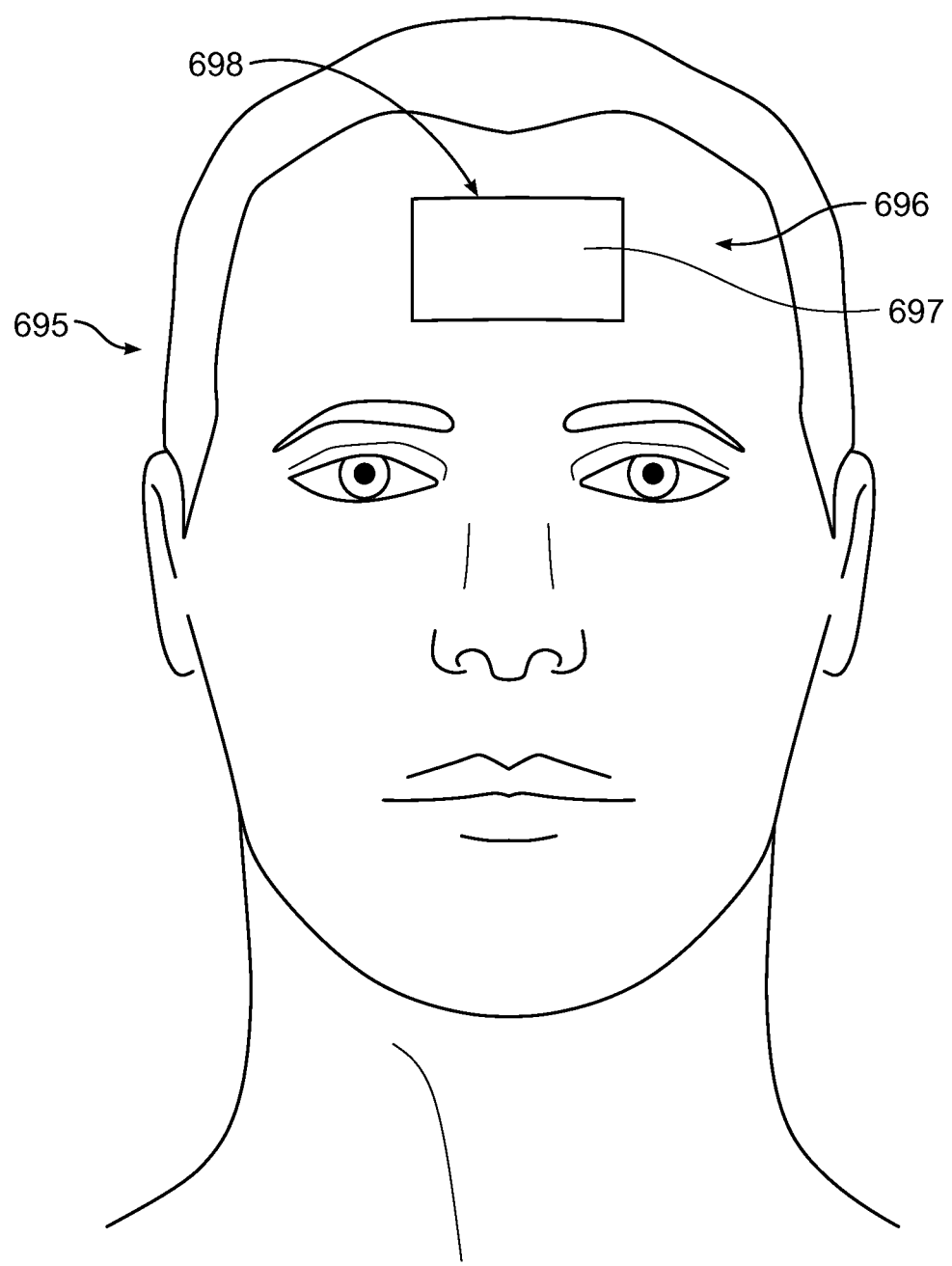

FIG. 6F shows a front view of a head 695 including a forehead 696. One of the embodiments of the present disclosure 697 can be positioned against the forehead 696 at 698.

Although all surfaces of the embodiments of the present disclosure can be applied to the skin surface of body parts or portions thereof to administer the pharmaceutically active agents included therein (e.g., CBD and menthol) for transdermal delivery into and through the tissues of the skin surface to bring about the intended local and/or systemic effect, the largest surfaces (e.g., surface areas 102 and 104 in FIG. 1, in FIG. 2A with surface areas 202 and 204 and in FIG. 2B and with surface areas 208 and 210) should preferably be placed against those skin surfaces including the embodiments of FIGS. 6A to 6F.

For embodiments that are placed on a body part (e.g., patch embodiments), the dosing time can range from about 30 minutes to about 12 hours, about 30 minutes to about 8 hours (based on in vitro testing), 30 minutes to about 2 hours or about 30 minutes to about 1 hour. The greater the amount of humectant (e.g., glycerin), the longer the maximum the therapeutic dosing time. The remainder can then be removed from the body part or skin surface thereof.

Another embodiment of the present disclosure relates to a composition containing particles which have a core containing a pharmaceutically active agent or a salt thereof coated with a barrier layer. The barrier layer is formed from a coating liquid that contains a least one water insoluble barrier forming component selected from a group consisting of ethyl cellulose, copolymers of acrylic and methacrylic esters and natural or synthetic waxes, and a plasticizer.

The amount of the pharmaceutically active agent administered may be dependent on the subject being treated, the severity of the disorder or condition, the rate of administration, the disposition of the compound and the discretion of the prescribing physician. However, an effective dosage is in the range of about 0.001 to about 100 mg. per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Any standard manufacturing procedure known in the art may be used to manufacture the transdermal delivery system, patch, vehicle or device of the present disclosure. For example, in a vessel blend all the pharmaceutically active agents (e.g., cannabinoids and menthol), a carrier solvent, an absorbent polymer (e.g., a superabsorbent polymer), a humectant and a surfactant and optionally a heat source material at a temperature of, for example, of 76° C. until homogeneous. Then the homogeneous blended mixture is applied to woven or nonwoven absorbent material including for example, gauze (e.g., cotton gauze). The woven or nonwoven absorbent material treated with the homogeneous blended mixture is then placed in a package embodiment of the present disclosure.

Figure 3C:
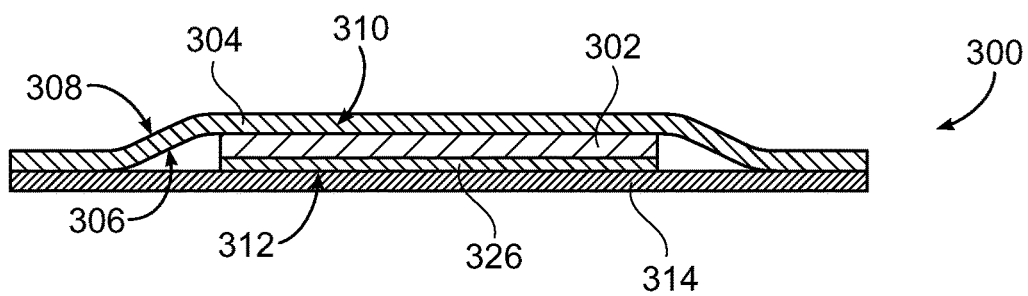

The embodiments of the present disclosure may also include a rate-controlling membrane 326 on the skin surface side of the transdermal delivery system, patch, vehicle or device of the present disclosure as shown in FIG. 3C and in substantial contact with the skin. The materials used to form such a membrane are selected to limit the flux of one or more components contained in the drug formulation, and the membrane may be either microporous or dense. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like.

Example 1

Ingredients: coconut oil 80.25 wt %; full spectrum hemp oil 5 wt %; menthol 0.25 wt %; NaCMC/croscarmellose 1.0 wt %; glycerin 3 wt %; polysorbate 80 0.5 wt %; and zeolite 10 wt %. The ingredients are blended together until homogeneous at about 76° C. Then 1 g. of the blend is applied to a 3M Tagaderm+pad.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:
1. A transdermal delivery system, comprising:
   a backing material includes a first side and a second side, the second side including a topically acceptable adhesive;
   an absorbent material layer that is a woven fabric or a non-woven fabric and includes a first side and a second side and wherein the first side of the absorbent material layer is positioned adjacent the second side of the backing material, the absorbent material including
      at least one hydrophobic pharmaceutically active agent;
      a carrier solvent consisting of coconut oil, shea butter or mixtures thereof in an amount of from 80 wt % to about 90 wt %;
      glycerin in an amount of from about 0.50 wt % to about 10.00 wt % wherein the glycerin has less than 0.5% residual water; and
   zeolite is in an amount of about 1.00 wt % to about 20.00 wt %;
      crosscarmellose sodium in an amount of from about 0.01 wt % to about 5.00 wt % wherein the crosscarmellose sodium has less than 0.5% residual water; and
   a release layer in contact with a portion of the second side of the backing material,
   wherein the absorbent material is positioned in a cavity in between the backing layer and the release layer and the second side of the absorbent material is configured to be in substantial contact with the skin surface of a user such that the at least one hydrophobic pharmaceutically active agent will pass through the second side of the absorbent material and contact the skin surface of a user.

2. The transdermal delivery system of claim 1, wherein the absorbent material further includes a surfactant.

3. The transdermal delivery system of claim 1, wherein the zeolite is a heat source material.

4. The transdermal delivery system of claim 1, wherein the at least one hydrophobic pharmaceutically active agent is selected from the group consisting of at least one cannabinoid, menthol and a combination thereof, wherein the at least one cannabinoid comprises cannabidiol or full spectrum hemp oil.

5. A method of treating at least one of pain and inflammation of an animal using a transdermal delivery system, the transdermal delivery system comprising:
    a backing material includes a first side and a second side, the second side including a topically acceptable adhesive;
    an absorbent material including a first side and a second side and wherein the first side of the absorbent material layer is positioned adjacent the second side of the backing material, the absorbent material including
    at least one cannabinoid;
    menthol;
    a carrier solvent consisting of coconut oil, shea butter or mixtures thereof in an amount of from 80 wt % to about 90 wt %;
    glycerin in an amount of from about 0.50 wt % to about 10.00 wt % wherein the glycerin has less than 0.5% residual water; and
    zeolite is in an amount of about 1.00 wt % to about 20.00 wt %;
    crosscarmellose sodium in an amount of from about 0.01 wt % to about 5.00 wt % wherein the crosscarmellose sodium has less than 0.5% residual water; and
    a release layer in contact with a portion of the second side of the backing material,
    wherein the absorbent material is positioned in a cavity in between the backing layer and the release layer and the second side of the absorbent material is configured to be in substantial contact with the skin surface of a user such that the at least one cannabinoid and menthol will pass through the second side of the absorbent material and contact the skin surface of a user,
    the method comprising:
    removing the backing material; and
    topically applying the first side of the absorbent material to a skin surface of a body part of the animal.

6. The method of claim 5, wherein the absorbent material further includes a humectant.

7. The method of claim 5, wherein the absorbent material further includes a heat source material.

8. The method of claim 5, wherein the carrier solvent is coconut oil, medium chain triglycerides, olive oil, castor oil, canola oil, triacetin, corn oil, petrolatum, mineral oil, shea butter or mixtures thereof.

9. The method of claim 5, wherein the at least one cannabinoid is full spectrum hemp oil.

10. The transdermal delivery system of claim 1, wherein the absorbent material layer is gauze.

* * * * *